(12) United States Patent
Laine et al.

(10) Patent No.: US 9,751,899 B2
(45) Date of Patent: *Sep. 5, 2017

(54) SYNTHESIS METHOD OF ALKOXYSILANES

(71) Applicants: Richard M. Laine, Ann Arbor, MI (US); Joseph C. Furgal, Ypsilanti, MI (US); Vera Popova, Ann Arbor, MI (US); Eongyu Yi, Ann Arbor, MI (US)

(72) Inventors: Richard M. Laine, Ann Arbor, MI (US); Joseph C. Furgal, Ypsilanti, MI (US); Vera Popova, Ann Arbor, MI (US); Eongyu Yi, Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/098,719

(22) Filed: Apr. 14, 2016

(65) Prior Publication Data
US 2016/0304540 A1    Oct. 20, 2016

Related U.S. Application Data

(60) Provisional application No. 62/147,637, filed on Apr. 15, 2015.

(51) Int. Cl.
  *C07F 7/08* (2006.01)
  *C07F 7/07* (2006.01)
  *C07F 7/04* (2006.01)

(52) U.S. Cl.
  CPC .............. *C07F 7/07* (2013.01); *C07F 7/045* (2013.01)

(58) Field of Classification Search
  CPC ................................ C07F 7/07; C07F 7/045
  USPC ........................................................ 556/446
  See application file for complete search history.

(56) References Cited

U.S. PATENT DOCUMENTS 5,099,052 A * 3/1992 Laine ................. C07F 5/069
                                                  544/181
8,475,758 B2    7/2013 Laine et al.
8,916,122 B2 * 12/2014 Laine ................... C07F 7/07
                                                  423/324

OTHER PUBLICATIONS

V. A. Weiss, G. Reiff, and A. Weiss, "Zur Kenntnis wasserbestandiger Kieselsaureester," Z Arong. Allg. Chem. 311, 142, 151 (1961).
C. L. Frye, "Pentacoodinate Silicon Derivatives. IV. Alkylammonium Siliconate Salts Derived from Aliphastic 1,2-Diols," J. Am. Chem. Soc. 92, 1205 (1970).
F. P. Boer, J. J. Flynn, J. W. Turley, "Structural Studies of Pentacoodinate Silicon. III. Tetramethylammonium Bis (o-phenylenedioxy) phenylsiliconate," J. Am. Chem. Soc. 90, 6973 (1968).

* cited by examiner

*Primary Examiner* — Sudhakar Katakam
*Assistant Examiner* — Kofi Adzamli
(74) *Attorney, Agent, or Firm* — Kubotera & Associates, LLC

(57) ABSTRACT

The direct depolymerization of biogenic and other high surface area silica sources uses both simple and hindered diols to produce alkoxysilanes in one or two steps that can be separated and purified directly from the reaction mixture by distillation, extraction or filtration followed by solution modification and distillation or extraction. The alkoxysilanes can take the form of spirosiloxanes or simple alkoxysilanes or oligomers thereof. Thereafter they can be treated with acid to produce colloidal or precipitated silica or aerosolized and combusted to provide fumed silica without the intervention of $SiCl_4$.

17 Claims, 5 Drawing Sheets

SYNTHESIS METHOD OF ALKOXYSILANES

BACKGROUND OF THE INVENTION AND RELATED ART STATEMENT

The present invention relates to a synthesis method of alkoxysilanes. In particular, the present invention relates to direct depolymerization of biogenic and other high surface area silica sources using both simple and hindered diols to produce alkoxysilanes in one or two steps that can be separated and purified directly from the reaction mixture by distillation, extraction or filtration followed by solution modification and distillation or extraction.

Although coal and crude oil make up less than 0.01% of the Earth's crust, their utility to society is enormous given that they serve as the basis for much of the world's fuel, for most organic materials ranging from plastic bags to fibers for textiles, to food packaging to major components in flat panel displays, etc. In contrast, silicon (as silica, $SiO_2$) lies just below carbon in the periodic chart, offers many chemical bonding similarities; makes up more than 40% of the Earth's minerals, and yet has much less impact on our society despite being important for applications ranging from solar cells to silicone rubbers to potential drug analogs (1).

In part this problem arises because unlike carbon, silicon-silicon and silicon-carbon double bonds are very hard to synthesize unless sterically stabilized and hence are not easily polymerized using the same chemistries as used for carbon. In part this problem also arises because the silicon-oxygen bond (534 KJ/mol) is one of the strongest bonds found in nature. Thus, most Si containing compounds and materials are produced from metallurgical grade silicon or $Si_{met}$, which is made by carbothermal reduction of silica with carbon in a high temperature, capital equipment and energy intensive process; see reactions (1)-(3). The much higher purities required for photovoltaic ($Si_{pv}$) and electronic ($Si_{eg}$) grade silicon require additional processing steps typically those of the Siemens process, reactions (5) and (6), which generate byproduct HCl, which is normally recycled.

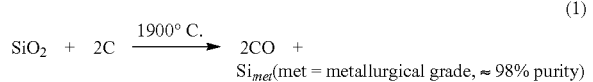

(1)

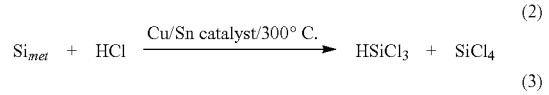

(2)

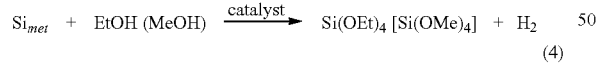

(3)

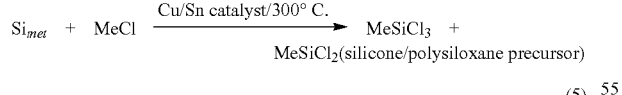

(4)

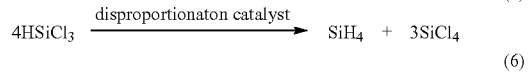

(5)

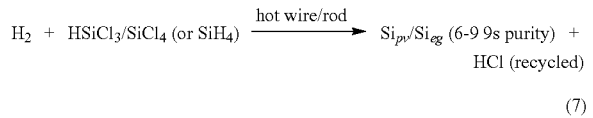

(6)

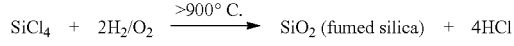

(7)

Nonetheless, because all chlorosilanes and HCl gas are corrosive, toxic and polluting, such production processes including those used to produce fumed silica (reaction 7) require expensive and extensive safeguards adding to the overall cost of the final products. Because $Si_{met}$ is a kinetic product, where SiC is the thermodynamic product; its synthesis requires electric arc furnace processing at ≈1900° C. adding to the overall cost even for $Si(OEt)_4$ or $Si(OMe)_4$.

Likewise, precipitated silicas are most commonly made via high temperature reaction of sand with sodium carbonate followed by dissolution and precipitation with $H_2SO_4$:

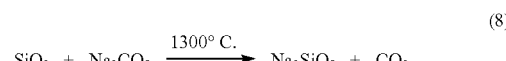

(8)

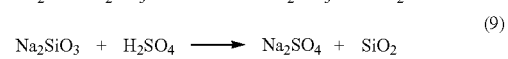

(9)

As can be seen, each mole of $Na_2SiO_3$ produced releases one mole of $CO_2$ and requires one mole of $H_2SO_4$ producing one mole of precipitated silica and one mole of $Na_2SO_4$, which must be disposed. Thus the production of precipitated (ppt) silicas such as used as filler in polymers (tires for example), as the abrasive in toothpaste, or in vacuum insulation panels also requires high temperatures and generates unwanted byproducts, especially $CO_2$ and $Na_2SO_4$ (1,4).

Reactions (1)-(7) begin with $SiO_2$, reduce it to the metal (e.g. $Si_{met}$) and then re-oxidize it back; often to some form of $SiO_2$ including fumed silica. This approach is illogical and because all these processes are equipment and energy intensive, it is unreasonably costly.

Thus, beginning in the early 30's, repeated attempts were made to develop low temperature, low cost methods of depolymerizing silica thereby generating alternate routes to silicon containing compounds as well as precipitated silica and more recently fumed silica. The success of such a process, as suggested by reaction (10) can be considered a "Grand Challenge" for silicon chemists. The idea of being able to distill the resulting product should allow the direct production of very high purity silicon containing materials including precipitated (ppt) $SiO_2$ directly from any silica source at low temperatures greatly reducing energy costs and the need for high capital equipment investments. There would also be a great advantage in producing fumed silica.

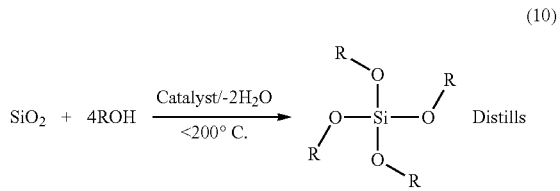

(10)

For example, high purity ppt or fumed silica is used in applications ranging from edible products (e.g. toothpaste) to polishing aids for planarizing silicon wafers to the production of high purity silica for optical applications (lenses, gratings, optical fibers, photonic band gap materials) to the production of crucibles for growing electronics grade silicon boules (1,4).

Thus researchers beginning in 1931 with Rosenheim et al (5), followed by Weiss et al (1961), (6) Frye (1964), (7) Boer et al (1968), (8,9) Barnum (1970), (9, 10) and Corriu (1986)

(11) explored SiO$_2$ depolymerization. This work covers a wide range of SiO$_2$ feedstocks from amorphous silica to quartz powder, but all of these studies focused on some form of reaction (11) generating hexacoordinated triscatecholato Si I (5-11).

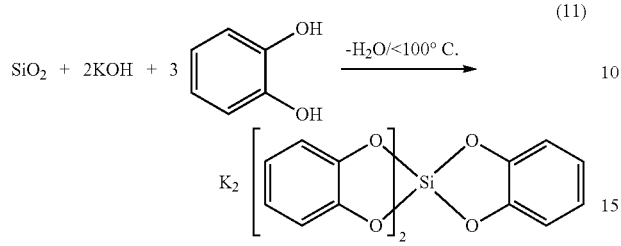

(11)

The key to the success of this reaction is the fact that silicon, unlike carbon, is able to form five and six bonds and thus the original Si—O bond strength of tetrahedral silicon is diminished. Unfortunately, I cannot be distilled and is so stable that it is water-soluble and would have to be reacted with H$_2$O$_4$ to produce ppt. SiO$_2$. From a practical perspective, this process while offering a low temperature route to ppt SiO$_2$ would require three moles of catechol per mole of ppt SiO$_2$ or ≈330 g of catechol to produce 60 g of ppt SiO$_2$ and coincidentally 280 g of Na$_2$SO$_4$. This is quite unattractive; although no CO$_2$ would be produced.

A search for something simpler than catechol led us to try ethylene glycol (ca 1988) to promote silica depolymerization according to reactions (12) and (13), (12, 13). The depolymerization mechanism again builds on expansion of the coordination sphere around silicon.

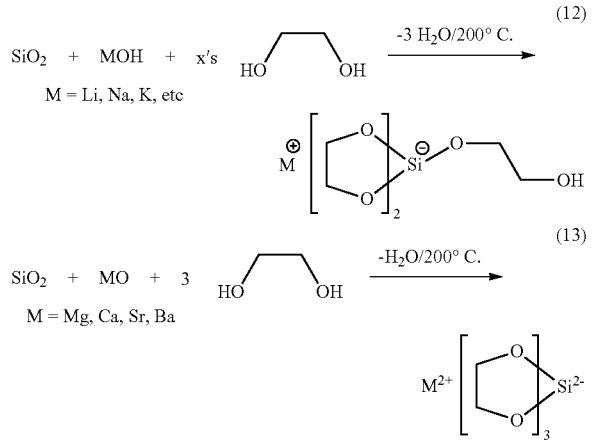

Still more recently, we were able to demonstrate that reaction (12) can be promoted catalytically using alkali base, reaction (14), (14,15). Our proof-of-principle studies were done with fumed silica (350 m$^2$/g), which defeats the overall objective of the "Grand Challenge;" however, these studies were important as they determined that: (1) reaction (14) is first order in base concentration and surface area; (2) the activation energy for the reaction is 60 kJ/mol; and (3) the reaction is faster with amorphous rather than crystalline silica (14). Unfortunately, the tetraglycoxysilane or GS cannot be distilled, it forms polymers [i.e. Si(eg)$_2$] on heating and is thus difficult to purify and therefore is again not a solution to the grand challenge although it is closer to what is desired.

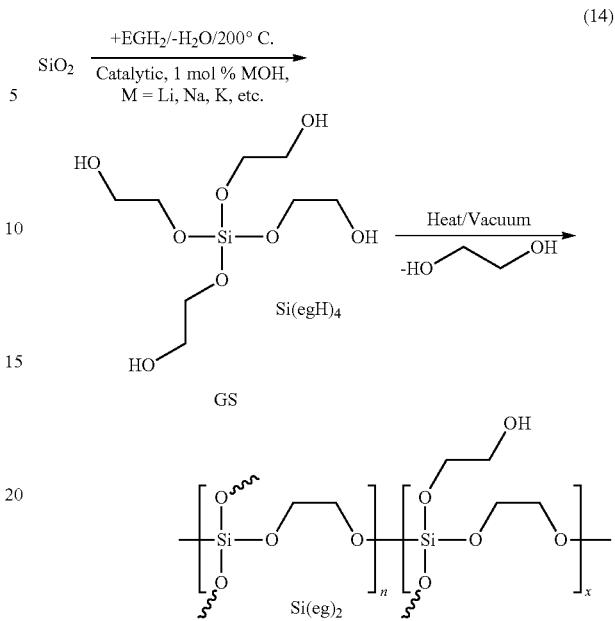

As a consequence, we sought amorphous biogenic silica sources with high surface areas identifying rice hull ash (RHA) and diatomaceous earth (DE) as reasonable replacements for fumed silica. RHA is produced in 250 k ton/yr quantities in the U.S. alone, is mostly amorphous and offers specific surface areas (SSAs) typically of ≈20-80 m$^2$/g. The samples used in our study are 70-90 wt % silica with 5-20 wt % carbon and 5 wt % minerals that are removed easily by washing with dilute HCl (16). We also were able to obtain a sample of rice hulls that had been ashed at ≥600° C. (A-RH) to produce a material that was >95 wt % silica and with SSAs≈230 m$^2$/g. DE is available from multiple sources with SSAs ranging from 1-70 m$^2$/g and is mostly amorphous.

Many plants ranging from diatoms to grasses to trees take soluble silica from water sources and transport it within their systems and deposit it in various forms and places ranging from the shells of diatoms, to the cells of hard woods, to rice hulls and stalks. In the majority of instances the transport systems involved in the biosilicification process are not designed to also transport heavy metals. Consequently biogenically deposited silica is relatively free of heavy metal impurities making it a prospective source for high purity silicon containing materials ranging from alkoxysilanes to silica to silicon nitride to silicon carbide to silicon metal. Biogenically produced silica can be defined as being a sustainable resource as for example in the case of any currently farmed silica accumulating plant. Their availability in industrially meaningful quantities as byproducts of existing human efforts to produce food and fiber makes this resource commercially important.

For example, rice hulls are produced in 100 million ton quantities annually world-wide as a generally undesirable byproduct of rice milling (17,18). They can contain 12-20 wt % silica in an amorphous, high surface area form. There are now multiple studies in the patent and open literature on the recovery of silicon containing materials from rich hulls. Thus, rice hulls and rice hull ash have been used as a starting point to make solar grade silicon, silicon carbide, silicon nitride and also to recover relatively pure silica through dissolution with a base such as alkali or alkaline earth carbonates or hydroxides, tetramethylammonium or choline hydroxide as noted in the following references and references used in these papers which are incorporated herein as prior art (1-18).

In a recent patent (U.S. Pat. No. 8,916,122), we described a method of producing alkoxysilanes and precipitated silicas from biogenic silicas and GS in particular. In a first step, biogenically concentrated silica is mixed with a liquid polyol and then is heated to distill out residual water. In a second step, a base is added and the reaction is heated to distill out the water that forms as shown in reactions (14) and (15).

In this patent it was suggested but never reduced to practice that it should be possible to produce distillable alkoxysilanes in the form of spirosiloxanes (19); however, this patent never discusses the production of simple alkoxysilanes such as TEOS.

SUMMARY OF THE INVENTION

Thus, in the current patent, we have explored and reduced to practice both synthesis methods. The diversion from the original patent is as follows:

At this juncture, processing can take one of two routes. In the simpler version, a spirosiloxane product, as suggested in

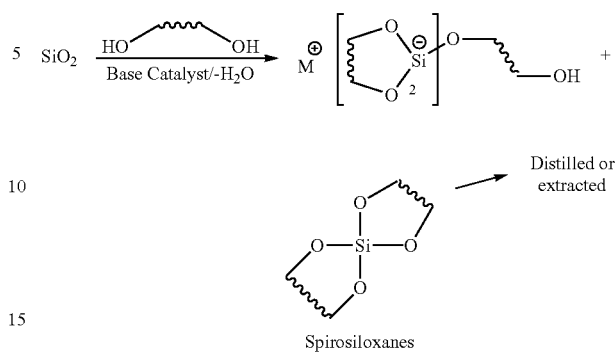

(15)

In this invention we demonstrate that it is possible to dissolve the silica in RHA or other biogenic sources of silica using a catalytic amount of base and a high boiling solvent that contains at least two hydroxyl groups capable of chelating the silicon atom as it is catalytically extracted from any silica surface to form a stable spirosiloxane or a polymeric analog as suggested in reactions (14)-(16).

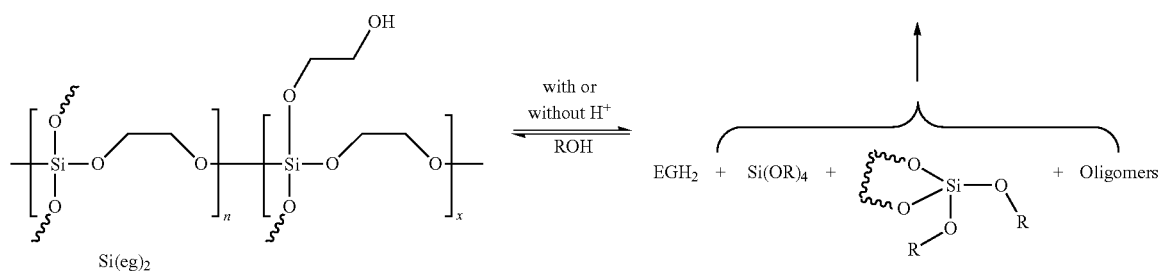

(16)

reaction (15), can be distilled directly from the reaction mixture if it has a boiling point below of near that of the liquid polyol. Alternately, for boiling points higher than the polyol, filtration removes the carbon enriched RHA or other undissolved biogenic silica to recover the solution of alkoxysilane, pentacoordinated silicate and polyol. Thereafter the formed alkoxysilane is purified by filtering if it forms a solid on cooling, distilling the polyol from the alkoxysilane, or by extraction from the original reaction solution using a solvent for the alkoxysilane that is a non-solvent for the polyol.

Still another method of separation not recognized previously is the use of a membrane that selectively passes the non-polar alkoxysilane but rejects the polar polyol and other reactants. Alternately, the residual base present in polyol/alkoxysilane solution is neutralized to eliminate the residual alkali metal base and the various purification processes as just noted can be conducted. The resulting solutions or spirosiloxanes can thereafter be treated to produce simple alkoxysilanes as detailed below.

Another important function of such a process would be to coincidentally, inexpensively and accurately reduce the total silica content in rice hull ash with the intent to precisely raise the relative carbon content as practiced in U.S. Pat. No. 8,475,758.

U.S. Pat. No. 8,916,122 suggests that it is possible to make spirosiloxanes from biogenic silicas but no examples were presented. In this patent, we provide examples of the synthesis of spirosiloxanes directly from biogenic silica but more importantly, we also provide examples of the direct and indirect synthesis of simple alkoxysilanes from the same sources and also demonstrate the production of fumed silica directly from both types of materials. Our processes are advantageous because they:

(1) greatly reduce the base needed to dissolve any biogenic silica but especially RHA;
(2) allow direct distillation of a spirosiloxane from the reaction solution without need for further filtration and recovery/purification thereafter;
(3) permit the transformation of glycoxysilanes, e.g. $Si[(CH_2CH_2O)_m(CH_2)_nOH]_4$ or $Si[CH_2(CH_2)nOH]_4$ (m, n=1-10) or its polymeric form for example $Si(eg)_2$ directly into easily separated alkoxysilanes such as $Si(OEt)_4$, TEOS.
(4) The direct use of either the spirosiloxane or TEOS for the production of colloidal, precipitated or fumed silica without first making $SiCl_4$.

All of these advantages provide lower cost materials, avoid high temperatures and excessive release of $CO_2$ and the need for costly capital equipment and high energy expenditures. Furthermore, the production of electricity coincident with the production of RHA makes these processes energy positive and since the energy comes from rice plants that take $CO_2$ out of the air to make carbon containing materials, the whole process is close to carbon neutral.

The examples of U.S. Pat. No. 8,916,122 provide the basic methods we use in the current discovery; however, some of the methods require modifications that are not obvious to one of average skill. The examples of Table 1 are conducted using standard conditions as listed. These conditions are meant to be exemplary rather than optimal. Some of the examples listed below involve larger scale efforts to demonstrate scalability and to explore partial optimization, which proves to be possible.

Table 1 also presents the characterization data for the starting materials that include both biogenic and mineral sources of silica, the reaction products and coincidentally compares the extent of dissolution using standard conditions listed. With the exception of vermiculite, all of the sources are amorphous silica. In general, the amount of $SiO_2$ that dissolves for all sources relates to specific surface areas, SSAs and reaction temperatures. Vermiculite's low silicon content and crystallinity are likely at least partially responsible for its poor dissolution rates.

spectral analyses suggest that the diol "cracks" producing propanol as the major product rather than the spirosiloxane II. Both DE and Celite likely have highly acidic sites that account for the observed cracking products. The ashed rice hulls give the second highest dissolution under standard conditions, as might be expected with SSAs of ≈230 $m^2/g$.

Vermiculite is a common aluminosilicate mineral with no free $SiO_2$ available for dissolution, yet some dissolution obtains. We have not characterized the product(s); although some alumina dissolution may occur concurrently given Al-EG complexes have been reported previously (20).

The distillation of 2-methyl-2,4-pentanediol and II occur at nearly the same temperature making isolation and purification somewhat problematic. However, we were pleasantly surprised to find that both II and 2-methyl-2,4-pentanediol are hexane soluble with the diol also being water soluble. Hence simply washing hexane solutions of the recovered, distilled mixture or the reaction filtrate removes the diol and leaves pure II, which is easily recovered and can be redistilled at ≈200° C. to give much higher purities. Simple rotary evaporation leads to II as a liquid that slowly crystallizes on cooling (21,22).

TABLE 1

Percent $SiO_2$ depolymerized; 0.3 mol $SiO_2$, 0.03 mol NaOH, 300 ml distilled, 4-8 h.

| | | | Diol (bp° C.) | | |
|---|---|---|---|---|---|
| $SiO_2$ | SSAs $m^2/g$ | $EGH_2$ (197°) | $HO(CH_2)_4OH$ (235°) | 2-methyl-2,4-pentanediol (197°) | 2,2,4-trimethyl-1,3-pentanediol (232°) |
| Celite | 1 | 12% | 13% | 4% | 1.5% |
| Vermiculite 4 | 2.5 | 3 | 3 | — | — |
| RHA | 26 | 20 | 23 | 24 | 12 |
| DE | 23 | 16 | 18 | 4 | 3 |
| Fumed $SiO_2$ | 350 | 98+ | 98+ | 98+ | 98+ |
| A-RH | 230 | | | 60 | — |
| Mass Spec.† | | Spiro 149, 80% intensity[23] | Spiro 205, 15% intensity | Spiro 260, I = 15% —$CH_3$ 245 100% | Spiro 316, I = 7% 273 (—$Me_2CH$) I = 30% |
| $^1$H (δ) | | Si(glycoxy)$_4$[23] C$\underline{H}_2$O 3.74 C$\underline{H}_2$OH 3.94 | C$\underline{H}_2$O 3.41, C$\underline{H}_2$ 1.45 Si(OROH)$_4$ C$\underline{H}_2$O 3.70 C$\underline{H}_2$ 1.65 | C$\underline{H}$OH 4.20, C$\underline{H}_2$ 1.47, 1.64 C$\underline{H}_3$ 1.30, 1.24, 1.18 II C$\underline{H}_2$O 4.30, C$\underline{H}_2$ 1.48, 1.66 C$\underline{H}_3$ 1.28, 1.22, 1.18, | C$\underline{H}$OH 3.7, C$\underline{H}_2$OH, 3.32, C$\underline{H}$ 1.87 C$\underline{H}_3$ 0.73, 0.75, 0.95, III C$\underline{H}$O 3.4, C$\underline{H}_2$O, 3.20, C$\underline{H}$ 1.59 C$\underline{H}_3$ 0.87, 0.88, 0.97, |
| $^{13}$C (δ) | | Si(glycoxy)$_4$[23] C$\underline{H}_2$O 3.74 C$\underline{H}_2$OH 3.94 | C$\underline{H}_2$O 62.55 C$\underline{H}_2$ 29.84 Si(OROH)$_4$ C$\underline{H}_2$O 64.80 C$\underline{H}_2$ 31.99 | $\underline{C}(Me)_2$OH 71.56, $\underline{C}(H,Me)$OH 65.64, C$\underline{H}_2$ 49.47 ($\underline{C}H_3)_2$ 31.82, 27,71, C$\underline{H}_3$ 24.31 II $\underline{C}(Me)_2$OH 74.63, 74.38 $\underline{C}(H,Me)$OH 67.82, 67.60 C$\underline{H}_2$ 48.40, 48.32 ($\underline{C}H_3)_2$ 32.20, 27.98 C$\underline{H}_3$ 24.17 | C$\underline{H}_2$OH, 83.11 $\underline{C}$HOH 73.3, $\underline{C}$ 39.04, $\underline{C}$H 29.08 $\underline{C}$H$_3$ 23.27, 19.66, 16.60, III $\underline{C}$HO 82.52, $\underline{C}$H$_2$O 69.17, $\underline{C}$ 40.80? $\underline{C}$H 30.57 $\underline{C}$H$_3$ 23.11, 18.72, 15.16 |
| $^{29}$Si (δ) | | −82 | −82 | −82 | −81.85 |

†MALDI, EI, FABS $^{29}$Si NMRs show GS is analogous to LEOS and Si(OBu—OH)$_4$ peak, spirosiloxane shifted.
$^1$H, $^{13}$C NMRs suggest chirality in spirosiloxanes, likely a racemic mixture.

Thus for all sources, $SiO_2$ depolymerization in 1,4-butanediol is greater than in $EGH_2$ (b.p. 200° C.) as the former boils some 40° C. higher than the latter. The depolymerization rates for 2-methyl-2,4-pentanediol (b.p. 200° C.) are similar but not quite as high as $EGH_2$. Dissolution of celite and diatomaceous earth are not always effective as mass Compound III and the parent diol are also hexane soluble but the diol is not water soluble; however, III can be isolated simply by washing with MeOH. Both spirosiloxanes can be distilled to higher purity. Both II and III are the first examples of a distillable form of silica made at low temperatures directly from biogenic silica.

What is not obvious in the Table 1 studies is that if one were to use 2-methyl-2,4-pentanediol as the diol under the stated reaction conditions but with a standard rice hull ash, the rate of dissolution would be closer to 45% (Example 1). This same rice hull ash treated under similar conditions but in $EGH_2$ undergoes silica dissolution in much shorter times but to the same conversions as demonstrated in Example 2. In this instance, the synthesis of spirosiloxane II for example is best done by adding 2-methyl-2,4-pentanediol to the already dissolved GS of Example 2.

Perhaps most important is that it is possible to isolate by filtration and concentrate GS per Reaction (14) and thereafter add methanol, ethanol or other simple alcohol to create an equilibrium as shown in reaction (16). Note that a different diol can be used in reactions like (16) as illustrated in the Table 1 examples. Thereafter, equilibration provides a significant amount of $Si(OR)_4$ that can be recovered in several ways.

The simplest method is simply to distill the product. The next simplest is to extract the $Si(OR)_4$ into hexanes or other hydrocarbon solvent and simply remove the solvent by evaporation. This can offer moderate to excellent yields as demonstrated in the examples. If the hydrocarbon phase and the alcohol phase are not miscible then the extraction of the $Si(OR)_4$ into the hydrocarbon phase can drive the reaction (16) equilibrium and more $Si(OR)_4$ can form and again be drawn into the hydrocarbon phase.

As an alternative, passing the solution through or immersing in the solution, a semipermeable membrane that is permeable only to $Si(OR)_4$ and not to the Si polymer of (16) or the ROH used in the equilibration process, then $Si(OR)_4$ can be drawn off as it forms and this will again drive equilibration. The latter two approaches have the advantage of minimizing the amount of ROH used in the exchange process. Note that the rate of equilibration will be improved if the process is acid or base catalyzed. The base that is already present in the original reaction solution will serve as a catalyst for equilibration as seen in Example 14. Alternately the addition of a non-aqueous acid or acid anhydride will catalyze the equilibration without also generating precipitated silica. The acid could be an organic acid or anhydride or HCl or $CO_2$ gas or other acid known to a general practitioner of the art of alkoxy exchange, e.g. in transesterification.

The recovered $Si(OR)_4$ can be further purified to a high degree by distillation. The resulting $Si(OR)_4$ or the originally recovered spirosiloxane can thereafter be combusted using a variety of methods as described in Example 15 but also by simple combustion in $H_2/O_2$ flames in the form as an aerosol. The advantage to the current approach is that the combustion process does not involve the use of toxic, polluting and corrosive $SiCl_4$ and therefore does not need the capital and equipment intensive methods inherent in the use of $SiCl_4$. Indeed, the 100 m long tube normally used with $SiCl_4$ can be replaced with a combustion tube of just a few meters long, e.g. 1-10 meters (23).

REFERENCES

1. Silicon and Silicon Alloys, Chemicals and Metallurgical, V. Dosaj, M. Kroupa, R. Bitta in Kirk-Othmer Encyclopedia of Chemical Technology. John Wiley & Sons, Inc. online.
2. M. Okamoto, E. Suzuki, Y. Ono, "Reaction Pathway of Formation of Methoxysilanes in the Reaction of Silicon with Methanol Catalyzed by Copper(I) Chloride," J. Catalysis, 1994 145, 537-543.
3. Kirk-Othmer Encyclopedia of Chemical Tech., 5th Ed. Vol. 22, pp 365-547 (2007).
4. J. Falcone, Silicon Compounds: Anthropogenic Silicas and Silicates," Kirk-Othmer Encyclopedia of Chemical Tech. DOI: 10.1002/0471238961.1925142006011203.a01.pub22005.
5. A. Rosenheim, B. Raibmann, G Schendel, "Über innerkomplexe Brenzcatchinate vierwertiger Elemente" Z. Anorg. Chem., 1931, 196, 160-176.
6. V. A. Weiss, G. Reiff, and A. Weiss, "Zur Kenntnis wasserbestandiger Kieselsaureester," Z. Anorg. Allg. Chem. 311, 142, 151 (1961).
7. F. P Boer, J. J. Flynn, J. W. Turley, "Structural studies of pentacoordinate silicon. III. Tetramethylammonium bis (o-phenylenedioxy)phenylsiliconate," J. Am. Chem. Soc. 90, 6973 (1968).
8. J. J. Flynn, F. P. Boer, "Structural Studies of Hexacoordinate Silicon. Tris(o-phenylenedioxy) siliconate," J. Am. Chem. Soc. 91, 5756 (1969).
9. D. W. Barnum "Catechol complexes with silicon," Inorg. Chem. 9, 1942 (1970).
10. D. W. Barnum, Reaction of Catechol with Colloidal Silica and Silicic Acid in Aqueous Ammonia," Inorg. Chem., 11 1424 (1970).
11. a. R. J. P Corriu, J. C. Young, Chemistry of Organic Silicon Compounds, S. Patai, Z. Rappaport, eds. Ch. 20, Wiley, Chichester, 1989. b. R. J. P. Corriu, "Some aspects of the reactivity of hypervalent species of silicon in organic synthesis" Pure and Appl. Chem. 60, 99 (1988).
12. R. M. Laine, K. Y. Blohowiak, T. R. Robinson, M. L. Hoppe, P. Nardi, J. Kampf, J. Uhm, "Synthesis of Novel, Pentacoordinate Silicon Complexes from $SiO_2$," Nature 353, 642 (1991).
13. M. L. Hoppe, R. M. Laine, J. Kampf, M. S. Gordon, L. W. Burggraf, "Barium Tris(glycolato)-silicate, a Hexacoordinate Alkoxy Silane Synthesized from $SiO_2$," Angew. Chem. Int. 32, 287 (1993).
14. a. H. Cheng, R. Tamaki, R. M. Laine, F. Babonneau, Y. Chujo, and D. R. Treadwell, "Neutral Alkoxysilanes from Silica," J. Am. Chem. Soc. 122, 10063 (2000).
15. C. R. Bickmore, M. L. Hoppe, R. M. Laine, "Processable Oligomeric and Polymeric Precursors to Silicates Prepared Directly from $SiO_2$, Ethylene Glycol and Base." in Synthesis and Processing of Ceramics: Scientific Issues, Mat. Res. Soc. Symp. Proc.; W. E. Rhine, T. M. Shaw, R. J. Gottschall, Y. Chen 249, 107 (1991).
16. R. M. Laine, D. J. Krug, J. C. Marchal, A. McColm, "Low cost routes to high purity silicon and derivatives thereof," U.S. Pat. No. 8,475,758 Jul. 2, 2013.
17. Sun, L.; Gong, K.; "Silicon-Based Materials from Rice Husks and Their Applications," Ind. Eng. Chem. Res.; (Review); 2001; 40(25); 5861-5877.
18. L. Sun, K. Gong, "Silicon-Based Materials from Rice Husks and Their Applications," Ind. Eng. Chem. Res. 40, 5861-5877 (2001).
19. C. L. Frye, "Stable Silicon Heterocyclic Derivatives of Branched Alkanediols," J. Org. Chem. 22, 2496 (1983).
20. a. B. Herreros, T. L. Barr, J. Klinowski, "Spectroscopic studies of barium aluminate glycolate, $Ba[Al_2(C_2H_4O_2)_4]$, a 5-coordinate aluminum compound," J. Phys. Chem. 98, 738 (1994).
21. M. Z. Asuncion, I. Hasegawa, J. Kampf, R. M. Laine, "The selective dissolution of rice hull ash to form $[OSiO_{1.5}]_8[R_4N]_8$ (R=Mc, $CH_2CH_2OH$) octasilicates. Basic nanobuilding blocks and possible models of intermediates formed during biosilification processes," Materials Chemistry 15, 2114-21 (2005).

22. Richard M. Laine, Phi Doan, Joseph C. Furgal, David Pan, Eongyu Yi and Vera Popova, "Distilling spirocyclic alkoxysilanes from biogenic, green and sustainable sources," Angewandte Angew. Chem. Int. Ed. 2015, 54, 1065-1069.
23. E. Yi, C. E. Hyde, K. Sun, and R. M. Laine, "Escaping Carbothermal Reduction. Fumed Silica From Sustainable, Green Sources Without First Having to Make $SiCl_4$," Chem. Eur. J. 2016, 22, 2257-2260.

BRIEF DESCRIPTION OF THE DRAWINGS

FIGS. 6(a), 6(b), and 6(c) are photographs showing TEM images of fumed $SiO_2$, wherein FIG. 6(a) is LF-FSP of compound I, FIG. 6(b) is LF-FSP of TEOS, FIG. 6(c) is commercial; and FIGS. 7(a) and 7(b) are graphs showing FTIR of fumed $SiO_2$, wherein FIG. 7(a) is LF-FSP, FIG. 7(b) is commercial.

DETAILED DESCRIPTION OF PREFERRED EMBODIMENTS

Hereunder, preferred embodiments of the present invention will be explained with reference to the accompanying drawings.

Example 1. 2-methyl-2,4-pentanediol Dissolution Reaction Just Run, ~45% Conversion RHA (1000 g, 85 wt. % silica content, 14.16 moles of silica) was dissolved in 10 L of 2-methyl, 2,4-pentanediol (hexylene glycol, HG) and placed in a 22 L flask, equipped with a heating mantle and a mechanical stirrer. Then, catalyst (10 mol. % NaOH) dissolved in 900 mL of ethanol was added to the reaction flask. The reaction mixture was slowly heated and refluxed for 2 days. Then the distillation started—first the ethanol/water was distilled out, and then the temperature was increased to start the SP/HG distillation. SP was distilled out and fresh HG added. The distillation was carried about 40 h and ~9 L of distilled SP was collected, and then worked up (addition of hexane and three water washing steps). After addition of hexane, the solution formed two immiscible layers (diol and hexane) that were separated prior the washing steps. Then the hexane layer (containing the spirosiloxane product) was washed with water three times, dried over sodium sulfate and collected. In the final step the hexane was removed on a rotary evaporator to yield the product (1624 g of spirosiloxane). This means that we were able to extract ~45% silica from the starting RHA. The theoretical yield for 45% silica dissolution is 1657 g (98% yield).

Example 2. Ethylene Glycol Dissolution Reaction Just Run With HG Added 40% Conversion RHA (630 g, 7.87 moles of silica) was placed in a 12 L flask, equipped with a heating mantle and a mechanical stirrer. Catalyst (10 mol. % NaOH) was added with 7 l of $EGH_2$ and distillation started. Silica dissolution rates are seen in Table 1.

TABLE 1

Percent silica dissolved (by LOI) from processed RHA with 10 mol. % NaOH.

| Time, h | Silica Dissolution |
|---|---|
| 6 | 28.2% |
| 12 | 31.7% |
| 18 | 35.4% |
| 24* | 37.1% |

*At 37% dissolution, the reaction was converted to synthesize spirosiloxane (SP).

Then, 3.5 L of 2-methyl, 2,4-pentanediol (hexylene glycol, HG) was added and spirosiloxane distillation commenced. SP was distilled out (~3 L) and collected, and then worked up (addition of hexane and three water washing steps). After addition of hexane, the solution formed two immiscible layers (diol and hexane) that were separated prior the washing steps. Then the hexane layer (containing the spirosiloxane product) was washed with water three times, dried over sodium sulfate and collected. In the final step the hexane was removed on a rotary evaporator to yield the product (spirosiloxane) giving ~507 g spirosiloxane (~80% yield).

Figure 1:
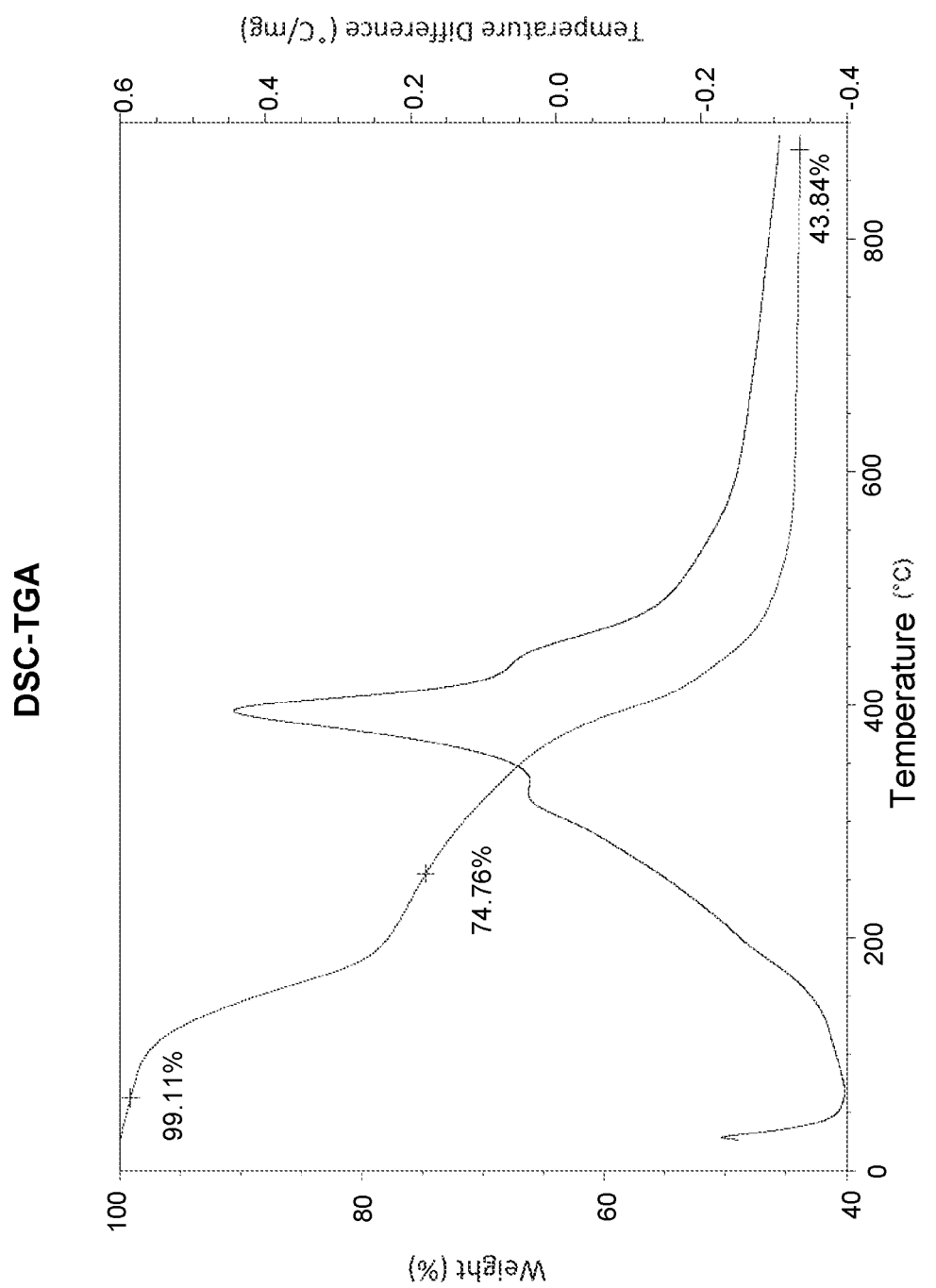
FIG. 1 is a graph showing TGA-DTA of silica depleted RHA after the work-up of spirosiloxane.
Figure 2:
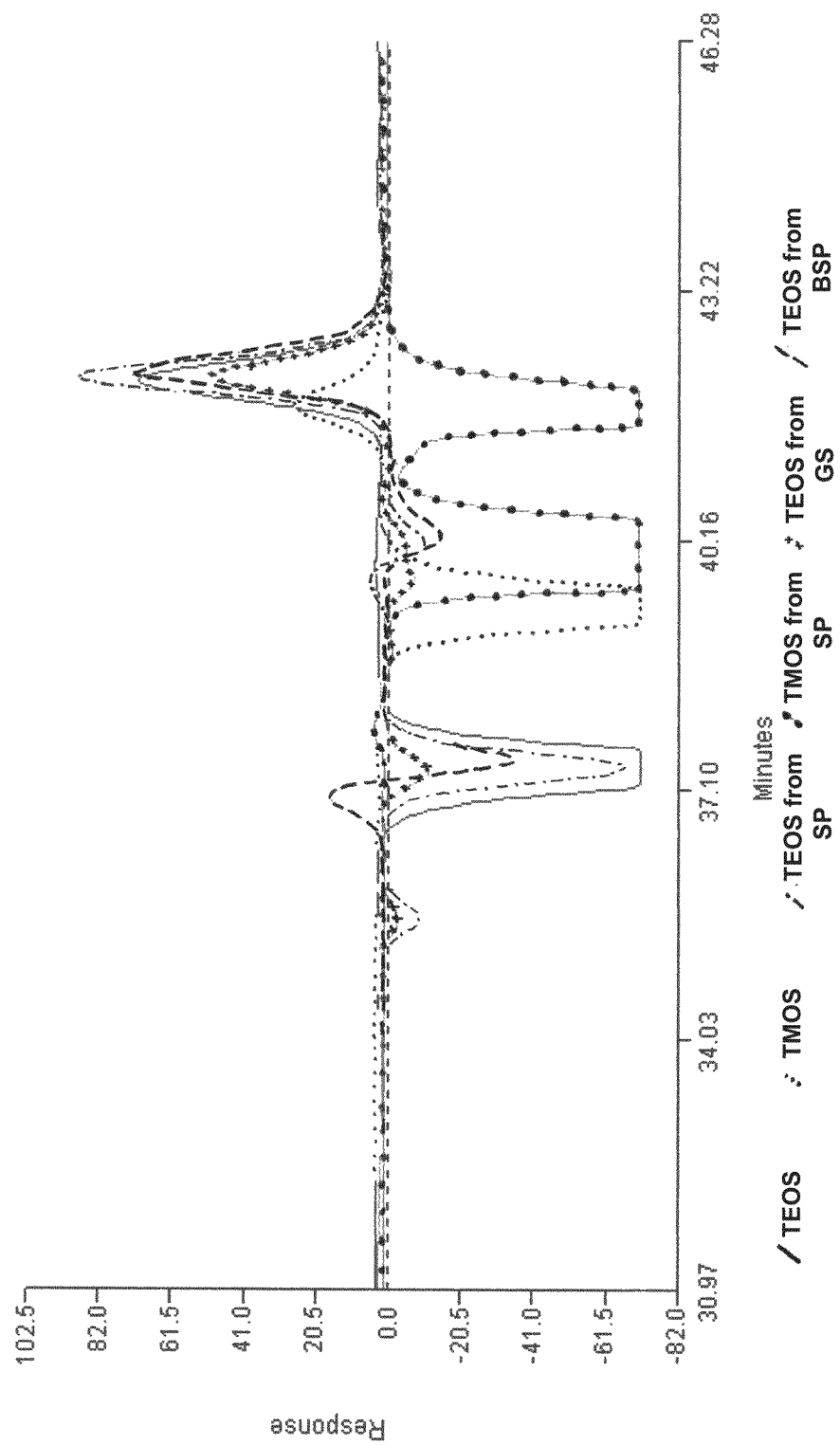
FIG. 2 is a graph showing GPC of tetraethoxysilane, Gelest; tetramethoxysilane, Sigma-Aldrich; TEOS from Si(2-methyl-2,4-pentanediolato)$_2$ (SP); TMOS Si(2-methyl-2,4-pentanediolato)$_2$ (SP); TEOS from glycoxysilane (GS); and TEOS from Si(1,4-butanediolato)$_2$ (BSP)

The remaining RHA was washed with ethanol and filtered off and analyzed by TGA-DTA, FIG. 1. TGA-DTA of RHA showed 43 wt. % silica content. This means that we were able to extract almost half of the silica from the starting RHA (74.9 wt. % silica content).

Example 3. Conversion of I to TEOS

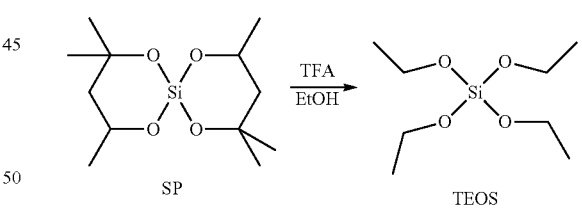

To a flame dried 500 mL round bottom flask equipped with magnetic stirrer under $N_2$ were added ~25 mL of activated 4 Å molecular sieves, 10 g (0.038 mol) of Si(2-methyl-2,4-pentanediolato)$_2$ (I), and 400 mL of dry 200 proof ethanol. The reaction mixture was allowed to stir for 1 h before addition of 2.5 mL (0.015 mol) of TFA. The reaction was left to stir at room temperature for 24 h. It was then filtered to remove molecular sieves and precipitated solids formed during the reaction process (ROP/silica byproducts). Then 400 mL of hexanes was added to the filtered solution and washed with water (3×150 mL) to remove TFA and diol. The pH of the resulting hexanes solution was then checked for neutrality. The hexanes solution was then dried over $Na_2SO_4$ and filtered. Then the solvent was removed in-vacuo, resulting in a colorless oil of Si(OEt)$_4$ as determined by GPC, yield 5.2 g, 65%.

Example 4. Conversion of I to TEOS

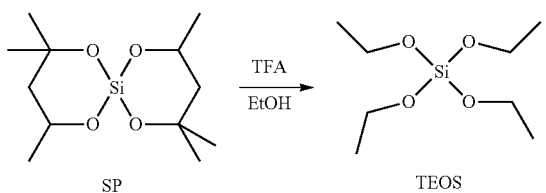

To a flame dried 250 mL round bottom flask equipped with magnetic stirrer under N$_2$ were added ~10 mL of activated 4 Å molecular sieves, 5 g (0.019 mol) of Si(2-methyl-2,4-pentanediolato)$_2$ (I), and 200 mL of dry 200 proof ethanol. The reaction mixture was allowed to stir for 1 h before addition of 0.625 mL (0.008 mol) of TFA. The reaction was left to stir at room temperature for 24 h. It was then filtered to remove molecular sieves and precipitated solids formed during the reaction process (ROP/silica byproducts). Then 800 mL of hexanes was added to the filtered solution and washed with water (3×300 mL) to remove TFA and diol. The pH of the resulting hexanes solution was then checked for neutrality. The hexanes solution was then dried over Na$_2$SO$_4$ and filtered. Then the solvent was removed in-vacuo, resulting in a colorless oil of Si(OEt)$_4$ as determined by GPC, yield 2.3 g, 63%.

Example 5. Conversion of I to TEOS

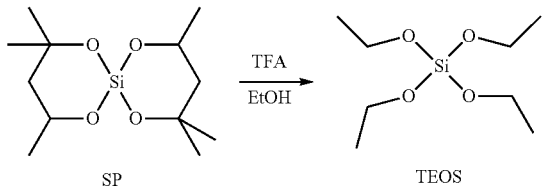

To a flame dried 250 mL round bottom flask equipped with magnetic stirrer under N$_2$ were added ~10 mL of activated 4 Å molecular sieves, 5 g (0.019 mol) of Si(2-methyl-2,4-pentanediolato)$_2$ (I), and 200 mL of dry 200 proof ethanol. The reaction mixture was allowed to stir for 1 h before addition of 0.45 mL (0.006 mol) of TFA. The reaction was left to stir at room temperature for 24 h. It was then filtered to remove molecular sieves and precipitated solids formed during the reaction process (ROP/silica byproducts). Then 400 mL of hexanes was added to the filtered solution and washed with water (3×150 mL) to remove TFA and diol. The pH of the resulting hexanes solution was then checked for neutrality. The hexanes solution was then dried over Na$_2$SO$_4$ and filtered. Then the solvent was removed in-vacuo, resulting in a colorless oil of Si(OEt)$_4$ as determined by GPC, yield 2.2 g, 61%.

Example 6. GS Conversion to TEOS

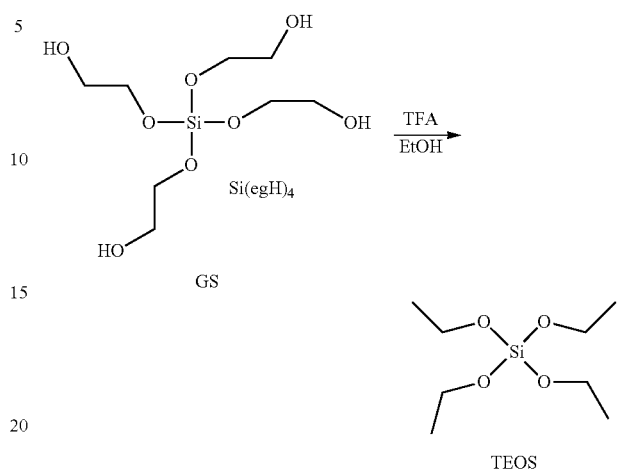

To a flame dried 500 mL round bottom flask equipped with magnetic stirrer under N$_2$ were added ~25 mL of activated 4 Å molecular sieves, 10 g (0.036 mol) of glycolato silicate (GS), and 400 mL of dry 200 proof ethanol. The reaction mixture was allowed to stir for 1 h before addition of 2.5 mL (0.015 mol) of TFA. The reaction was left to stir at room temperature for 24 h. It was then filtered to remove molecular sieves and precipitated solids formed during the reaction process (ROP/silica byproducts). Then 800 mL of hexanes was added to the filtered solution and washed with water (3×300 mL) to remove TFA and diol. The pH of the resulting hexanes solution was then checked for neutrality. The hexanes solution was then dried over Na$_2$SO$_4$ and filtered. Then the solvent was removed in-vacuo, resulting in a colorless oil of tetraethoxysilane. Crude yield 2.5 g, 40%.

Example 7. GS Conversion to TEOS

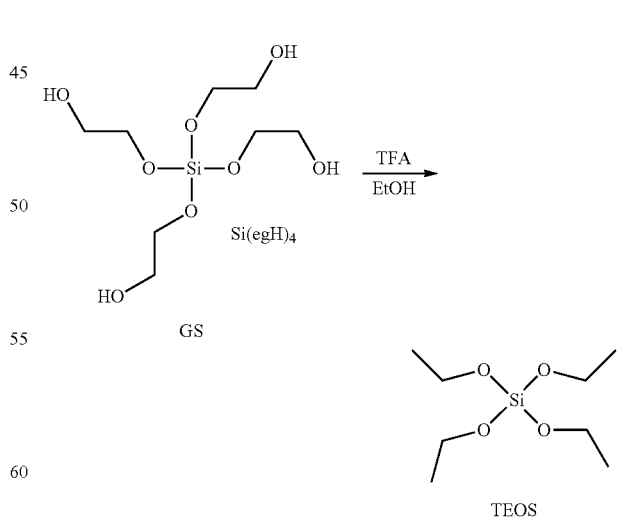

To a flame dried 250 mL round bottom flask equipped with magnetic stirrer under N$_2$ were added ~10 mL of activated 4 Å molecular sieves, 5 g (0.018 mol) of glycolato silicate (GS), and 200 mL of dry 200 proof ethanol. The reaction mixture was allowed to stir for 1 h before addition of 0.625 mL (0.008 mol) of TFA. The reaction was left to stir at room temperature for 24 h. It was then filtered to remove molecular sieves and precipitated solids formed during the reaction process (ROP/silica byproducts). Then 400 mL of hexanes was added to the filtered solution and washed with water (3×150 mL) to remove TFA and diol. The pH of the resulting hexanes solution was then checked for neutrality. The hexanes solution was then dried over Na₂SO₄ and filtered. Then the solvent was removed in-vacuo, resulting in a colorless oil of tetraethoxysilane. Crude yield 1.46 g, 40%.

Example 8. GS Conversion to TEOS

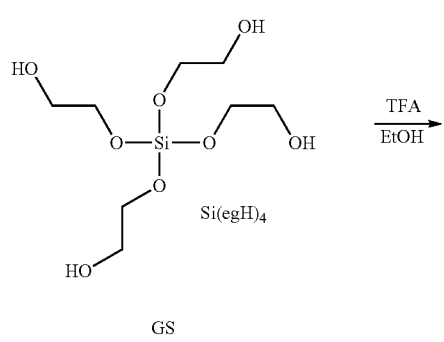

To a flame dried 250 mL round bottom flask equipped with magnetic stirrer under N₂ were added ~10 mL of activated 4 Å molecular sieves, 5 g (0.018 mol) of glycolato silicate (GS), and 200 mL of dry 200 proof ethanol. The reaction mixture was allowed to stir for 1 h before addition of 0.45 mL (0.006 mol) of TFA. The reaction was left to stir at room temperature for 24 h. It was then filtered to remove molecular sieves and precipitated solids formed during the reaction process (ROP/silica byproducts). Then 400 mL of hexanes was added to the filtered solution and washed with water (3×150 mL) to remove TFA and diol. The pH of the resulting hexanes solution was then checked for neutrality. The hexanes solution was then dried over Na₂SO₄ and filtered. Then the solvent was removed in-vacuo, resulting in a colorless oil of tetraethoxysilane. Crude yield 2.1 g, 56%.

Example 9. GS Conversion to TEOS

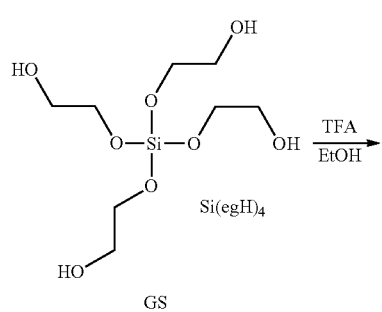

-continued

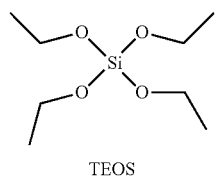

To a flame dried 250 mL round bottom flask equipped with magnetic stirrer under N₂ were added ~10 mL of activated 4 Å molecular sieves, 5 g (0.018 mol) of glycolato silicate (GS), and 75 mL of dry 200 proof ethanol. The reaction mixture was allowed to stir for 1 h before addition of 0.625 mL (0.008 mol) of TFA. The reaction was left to stir at room temperature for 24 h. It was then filtered to remove molecular sieves and precipitated solids formed during the reaction process (ROP/silica byproducts). Then 400 mL of hexanes was added to the filtered solution and washed with water (3×150 mL) to remove TFA and diol. The pH of the resulting hexanes solution was then checked for neutrality. The hexanes solution was then dried over Na₂SO₄ and filtered. Then the solvent was removed in-vacuo, resulting in a colorless oil of tetraethoxysilane. Crude yield 1.4 g, 40%.

Example 10. GS Conversion to TEOS

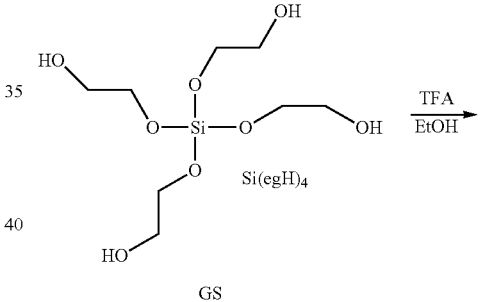

To a flame dried 250 mL round bottom flask equipped with magnetic stirrer under N₂ were added ~10 mL of activated 4 Å molecular sieves, 5 g (0.018 mol) of glycolato silicate (GS), and 75 mL of dry 200 proof ethanol. The reaction mixture was allowed to stir for 1 h before addition of 0.625 mL (0.008 mol) of TFA. The reaction was left to stir at room temperature for 24 h. It was then filtered to remove molecular sieves and precipitated solids formed during the reaction process (ROP/silica byproducts). Then 400 mL of hexanes was added to the filtered solution and washed with water (3×150 mL) to remove TFA and diol. The pH of the resulting hexanes solution was then checked for neutrality. The hexanes solution was then dried over Na₂SO₄ and filtered. Then the solvent was removed in-vacuo, resulting in a colorless oil of tetraethoxysilane. Crude yield 2.1 g, 55%.

Example 11. (Butanediolato)$_4$Si Conversion to TEOS

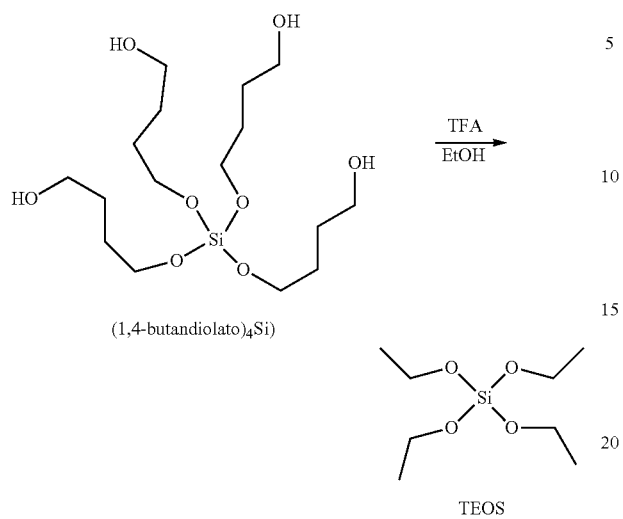

(1,4-butandiolato)$_4$Si)

TEOS

To a flame dried 500 mL round bottom flask equipped with magnetic stirrer under N$_2$ were added ~25 mL of activated 4 Å molecular sieves, 10 g (0.026 mol) of Si(1,4-butanediolato)$_4$ (BSP), and 400 mL of dry 200 proof ethanol. The reaction mixture was allowed to stir for 1 h before addition of 2.5 mL (0.015 mol) of TFA. The reaction was left to stir at room temperature for 24 h. It was then filtered to remove molecular sieves and precipitated solids formed during the reaction process (ROP/silica byproducts). Then 800 mL of hexanes was added to the filtered solution and washed with water (3×300 mL) to remove TFA and diol. The pH of the resulting hexanes solution was then checked for neutrality. The hexanes solution was then dried over Na$_2$SO$_4$ and filtered. Then the solvent was removed in-vacuo, resulting in a colorless oil of tetraethoxysilane. Crude yield 710 mg, 14%.

Example 12. I Conversion to TMOS (Biphase System)

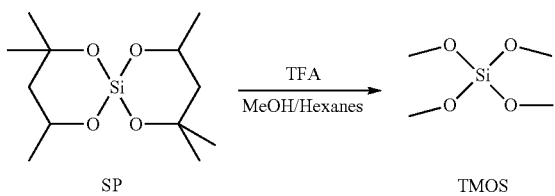

SP

TMOS

To a flame dried 500 mL round bottom flask equipped with magnetic stirrer under N$_2$ were added ~25 mL of activated 4 Å molecular sieves, 10 g (0.038 mol) of Si(2-methyl-2,4-pentanediolato)$_2$ (SP), and 200 mL of dry methanol and 200 mL of dry hexanes (an immiscible mixture). The reaction mixture was allowed to stir for 1 h before addition of 2.5 mL (0.015 mol) of TFA. The reaction was left to stir at room temperature for 24 h. The mixture was then poured into a separatory funnel and the two layers were separated. The hexane layer was then filtered and washed with water (3×300 mL) to remove TFA and residual diol. The pH of the resulting hexanes solution was then checked for neutrality. The hexanes solution was then dried over Na$_2$SO$_4$ and filtered. Then the solvent was removed in-vacuo, resulting in a colorless oil of tetramethoxysilane. Crude yield 3 g, 40%.

Example 13. Conversion of GS to TMOS+Oligomers

To a dry 1000 mL round bottom flask equipped with magnetic stirrer were added 50 g (0.03 mol) of glycolato silicate (16.3 wt. %), and 300 mL of anhydrous methanol. Then 300 mL of hexane were added to the reaction mixture. The reaction was left to stir at room temperature for 24 h. Then the hexane and methanol layers were separated in a sep-funnel and the hexane layer was washed with distilled water (3×300 mL) to remove the diol. The hexane solution was then dried over Na$_2$SO$_4$ and filtered. Then the solvent was removed in-vacuo, resulting in a colorless oil of tetramethoxysilane.

Figure 3:
FIG. 3 is a photograph showing that colloidal silica at pH 1 is transparent with no light scattering.
Figure 4:
FIG. 4 is a photograph showing that gelled silica at pH 7 after neutralization with $Na_2CO_3$ and for standing 30 min shows extensive scattering but likely due to bubbles.

Example 14. Conversion of Si(2-methyl-2,4-pentanediolato)$_2$ to Colloidal or Precipitated Silica To a 250 mL round bottom flask equipped with magnetic stirrer were added 10 g (0.038 mol) of Si(2-methyl-2,4-pentanediolato)$_2$, 50 mL of 200 proof ethanol, 4 mL of H$_2$O and 2 mL of 12N HCl such that the pH is <3. The reaction was left to stir at room temperature for 24 h, resulting in a transparent colloidal dispersion of silica particles as indicated by the lack of laser light scattering in FIG. 3. The colloidal silica appears to be stabilized by the presence of the 2-methyl-2,4-pentanediol. Addition of Na$_2$CO$_3$ to neutralize the solution results in slow gelation, FIG. 4. Alternately, the additional ethanol or hexanes causes silica to precipitate rather than gel as the 2-methyl-2,4-pentanediol appears to be solvated and removed from the silica surface.

Example 15. Fumed Silica

Spirosiloxane I was synthesized using the method described above. Distilled I was used for all the following experiments. TEOS was prepared as in Example 3. Methanol, ethanol, and propanol were purchased from Decon Labs (King of Prussia, Pa.). TEOS was purchased from Sigma-Aldrich (Milwaukee, Wis.).
LF-FSP.

Methanol, ethanol or propanol solutions of I and TEOS were obtained by dissolving sufficient I and TEOS to make a 1, 3 or 5 wt % silica ceramic yield solution. The general methods for conducting LF-FSP have been described in references x, y, z.

Figure 5:
FIG. 5 is a photograph showing that addition of 10 mL of ethanol to silica at pH 7, shows scattering from disruption of diol chelation.
Figure 6:
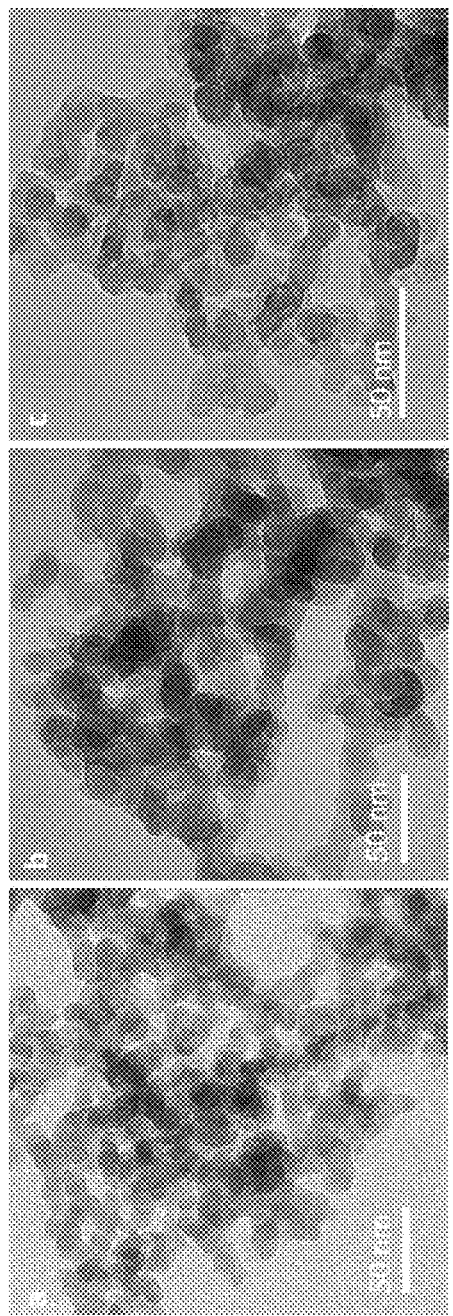
Figure 7:
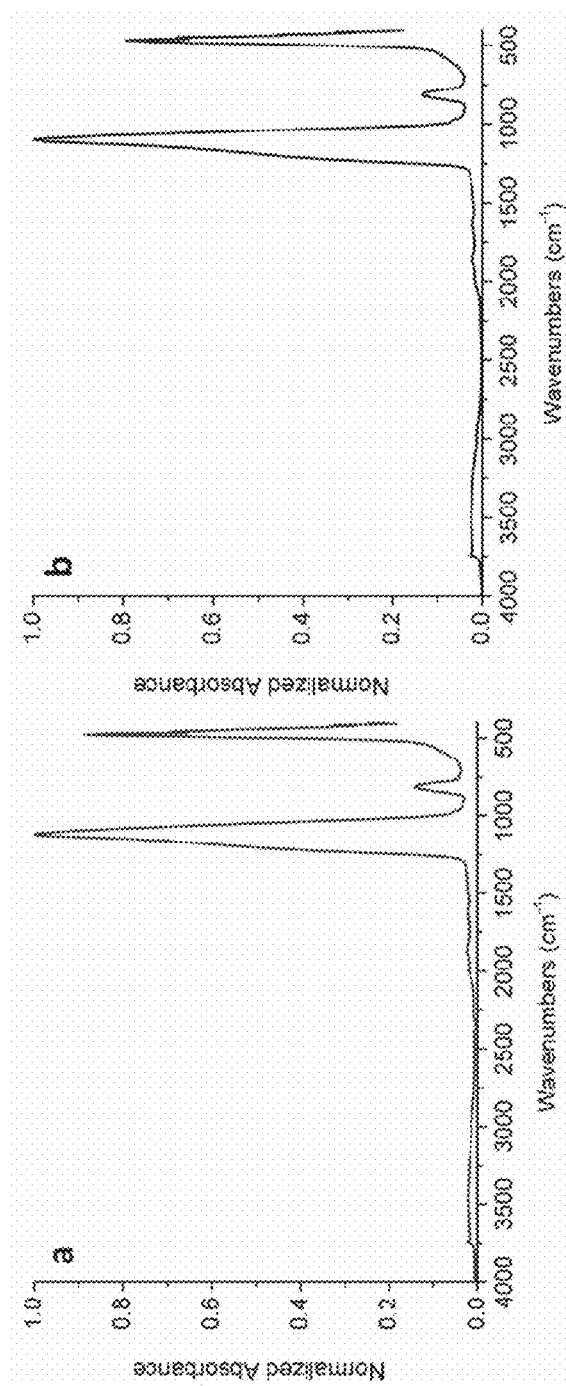

The properties of the as-produced fumed silica are identical to those of SiCl$_4$ derived silica and typical particle sizes are as shown in Table 2. Comparative transmission electron micrographs of the silicas are shown in FIG. 5. Comparative FTIRs for fumed silica produced from I and SiCl$_4$ are shown in FIGS. 6(a), 6(b), and 6(c).

TABLE 2

SSA of LF-FSP produced silica.

| Precursor | Solvent/Fuel | Precursor concentration (wt %) | SSA (m$^2$/g) |
|---|---|---|---|
| SS | MeOH | 1 | 230 |
|  |  | 3 | 190 |
|  | EtOH | 1 | 220 |
|  |  | 3 | 190 |
|  |  | 5 | 140 |
|  | PrOH | 1 | 210 |

TABLE 2-continued

SSA of LF-FSP produced silica.

| Precursor | Solvent/Fuel | Precursor concentration (wt %) | SSA (m$^2$/g) |
|---|---|---|---|
| TEOS | EtOH | 1 | 230 |
|  | EtOH | 3 | 180 |
|  | EtOH | 5 | 150 |

What is claimed is:

1. A synthesis method of alkoxysilanes, comprising:
   a first step, in which freshly produced or aged biogenically concentrated silica in a milled or un-milled form is mixed with a liquid polyol including ethylene glycol, 1,2-diol, 1,3-diol, 2,3-diol, 1,4-diol, triols, triethanolamine, trishydroxy-methylamine, or a mixture thereof;
   a second step, in which sufficient base including LiOH, NaOH, KOH, CsOH, RbOH or a mixture thereof in a catalytic amount ranging from 0.25-50 mol % is added so that a mixture is heated to a temperature where water and a by-product of a dissolution process distill out;
   a third step, in which addition of a diol that forms a 4,5 or 6 member ring with silicon forms an alcoholate and a spirosiloxane that is distilled out directly from the polyol solution before or after filtration to remove undissolved biogenic silica to recover the solution of alkoxysilane and the alcoholate substantially free of solids followed by distillation, extraction, or separation through a semipermeable membrane that selectively removes the spirosiloxane leaving anionic and polyol species to remain in the original reaction mixture followed by addition of simple ROH alcohols including MeOH and EtOH and stirred to effect exchange with the chelating diol to produce Si(OR)$_4$ which can be separated, being also possible to slightly acidify the solution using an organic acid or acid anhydride or non-aqueous inorganic acid or acid anhydride or ion exchange resin or HCl to catalyze the exchange reaction followed by purification, said recovered spirosiloxane or alkoxysilane then being combusted to produce fumed silica or treated with sufficient acid to produce colloidal dispersions of or precipitated silica; and
   a fourth step, in which any residual base present as alcoholate in the recovered alkoxysilane or rice hull ash is neutralized by adding a non-aqueous acid including HCl gas and NH$_4$Cl to eliminate the residual alkali metal base present in the form of a salt that can be removed by filtration or precipitation leaving a pure alkoxysilane or spirosiloxane free of metal impurities; alternately these impurities can be removed using ion exchange materials.

2. The synthesis method according to claim 1, wherein no additional base is added.

3. The synthesis method according to claim 1, wherein additional base is added.

4. The synthesis method according to claim 1, wherein NaOH or KOH is used.

5. The synthesis method according to claim 1, wherein a 1,2-diol, 2,3 or 1,3-diol or 1,4 diol is used to produce tetraglycoxysilanes and/or spirosiloxanes and the solution is concentrated to remove solvent.

6. The synthesis method according to claim 1, wherein a simple alcohol ROH is added to the filtrate before or after concentration and equilibrated and any product Si(OR)$_4$ is then recovered by distillation, extraction with a solvent that is a non-solvent for the filtrate medium or by membrane selective separation.

7. The synthesis method according to claim 1, wherein the solution is subsequently acidified using an anhydrous acid or acid anhydride or ion exchange resin to a nominal pH of 2-6.8 to promote formation of tetraalkoxysilanes and/or spirosiloxanes that thereafter can be further purified by distillation or extraction with a solvent that is a non-solvent for the filtrate medium or by membrane selective separation.

8. The synthesis method according to claim 1, wherein reaction is effected at temperatures of 140-250° C. at atmospheric pressure but preferably at temperatures of 160-220° C.

9. The synthesis method according to claim 1, wherein a second liquid such as benzene or toluene for example is used that can azeotrope water formed during the reaction such that the reaction temperature can be substantially reduced from the boiling point of the diol chosen.

10. The synthesis method according to claim 1, wherein reaction is effected at temperatures of 140-250° C. under pressures of 2-200 atmospheres but preferably 2-50 atmospheres and most preferable at 2-15 atmospheres.

11. The synthesis method according to claim 1, wherein the recovered spirosiloxane or alkoxysilane is combusted in the gas phase to produce fumed silica.

12. The synthesis method according to claim 1, wherein the recovered spirosiloxane or alkoxysilane is combusted in the gas phase to produce fumed silica.

13. The synthesis method according to claim 1, wherein the recovered spirosiloxane or alkoxysilane is treated with sufficient water and acid to produce a pH sufficient (<4) to stabilize a colloidal dispersion of silica.

14. The synthesis method according to claim 1, wherein the extracted alkoxysilane is treated with sufficient water and acid to produce a pH sufficient (<4) to stabilize a colloidal dispersion of silica.

15. The synthesis method according to claim 1, wherein the recovered spirosiloxane or alkoxysilane is treated with sufficient water and acid to produce a pH sufficient (<4) to precipitate the silica.

16. The synthesis method according to claim 1, wherein the recovered spirosiloxane or alkoxysilane is treated with sufficient water and acid to produce a pH sufficient (<4) to precipitate the silica.

17. The synthesis method according to claim 1, wherein the acid or acid anhydride used is nonaqueous for example HCl, CO$_2$, trifluoroacetic acid or anhydride or other common anhydrous organic acid or acid anhydride such that no water is introduced and the acidity is insufficient to cleave CH$_2$OH bonds to generate water unless precipitated or colloidal silica is desired.

\* \* \* \* \*